United States Patent [19]

Senn et al.

[11] Patent Number: 4,492,227
[45] Date of Patent: Jan. 8, 1985

[54] ELASTIC KNEE BANDAGE

[75] Inventors: Urs Senn, Basel; Bernhard Segesser, Riehen, both of Switzerland

[73] Assignee: Senn & Co. AG, Basel, Switzerland

[21] Appl. No.: 496,851

[22] Filed: May 23, 1983

[30] Foreign Application Priority Data

May 27, 1982 [CH] Switzerland ............... 3270/82

[51] Int. Cl.³ ............................................. A61F 13/00
[52] U.S. Cl. ................................. 128/165; 128/80 C
[58] Field of Search ............... 128/80 C, 87 R, 165, 128/82, 83; 2/22, 24

[56] References Cited

U.S. PATENT DOCUMENTS

| | | | |
|---|---|---|---|
| 3,831,467 | 8/1974 | Moore | 128/80 C |
| 3,934,583 | 1/1976 | Hollingshead et al. | 128/165 |
| 3,945,046 | 3/1976 | Stromgren | 128/165 X |
| 4,296,744 | 10/1981 | Palumbo | 128/80 C |

Primary Examiner—John D. Yasko
Attorney, Agent, or Firm—Ladas & Parry

[57] ABSTRACT

A tubular base body (1), made from an elastic textile material, has, in its central zone (II), a greater elastic stretchability than in the two adjacent rim zones (I and III). A stabilization zone (4) inclined by 15° to 45° relative to the main axis (A) is fitted on each flank, so that, in a front view, the two stabilization zones coverge in the shape of a V below the knee.

The upper section (I) of the base body preferably has a considerably greater length (H) than the lower section (h), and this results in excellent resistance to sliding, in interaction with the holding strips (2,3) provided in the rim zone and with the different stretchability of the three zones mentioned.

The knee bandage which can be used both for an injured knee and for a healthy knee is deliberately designed to fulfil the three functions of stabilization, guiding and warming of the knee region.

12 Claims, 4 Drawing Figures

ELASTIC KNEE BANDAGE

The invention relates to a knee bandage having a tubular base body which consists at least partially of an elastic textile material and comprises a central region which is to be laid against a knee joint, as well as two edge sections which adjoin this central region on both sides and the stretch properties of which differ from those of the central region.

Knee bandages of this type are used, for example, in the case of injuries to the knee joint, and in the case of degenerative changes in the joint, or even on a healthy knee for stabilising, guiding and warming it. It is particularly important here that the knee bandage does not slide when the knee is bent repeatedly, and does not form an obstacle in the hollow of the knee, that additionally a considerable warming action is provided in the region of the knee joint, and moreover, the construction and arrangement of the knee bandage result in an external stabilisation of the passive structure of the ligament system of the capsula of the knee, while providing the highest possible wearing comfort.

Known knee bandages of this type cannot meet these requirements to a satisfactory extent, and the disadvantages are in particular that all of them consist of a textile material that is only unidirectionally elastic, that is to say in the transverse direction, that they are also not resistant to sliding, and that their stabilisation zones, if these are provided at all, attempt to imitate the natural run of the ligaments, which—contrary to an existing prejudice in expert circles—does not permit optimum stabilisation of the knee region.

A bandage of the type defined above is known from German Offenlegungsschrift No. 3,028,381. The central region, to be laid against a knee joint, of this known bandage is designed in such a way that, as compared with the adjoining edge sections which surround the soft parts, it should generate substantially increased elastic tension and additionally have a lower elasticity. This tension in the central region covering the joint is intended to exert a high compressive force surrounding the knee joint on all sides. By the compressive action on the natural ligaments, the latter are to be supported. Although the range of motion of the natural ligament run can be restricted by means of compression, such compression measures do not provide real support with simultaneous, relatively free mobility of the ligaments.

It is thus the object of the present invention to provide an elastic knee bandage of the abovementioned type, which permits the said disadvantages of the known bandages to be overcome and accordingly, in particular in addition to an unusual resistance to sliding and an improved warming action, achieves a "rotational stabilisation" of the knee, whereby a "rotary" movement of the knee in a horizontal plane extending transversely to the vertical, is virtually prevented, but at least greatly reduced, and the injured knee, or the knee to be protected, is thus securely supported and guided.

This object is achieved by a knee bandage which is defined in the independent patent claim.

In the bandage according to the invention, the knee joint is surrounded by a central bandage region having an elasticity which in total is greater than that of the edge sections. This central region therefore does not exert any significant compressive action on the joint, but surrounds it on all sides with a relatively light tension. Due to their special alignment, the zones, provided according to the invention, for stabilising the joint flanks serve to provide true support of the joint, above all in the case of rotational movement. Because of the alignment of the stabilising zones, as carried out according to the invention, this advantageous supporting action is retained in an optimum manner over the entire course of movement of the joint.

British Patent Specification No. 1,515,153 has disclosed a knee bandage, the bandage body of which is provided with stiffening bands which cross each other below the knee joint. These bands, however, do not exert any supporting function like that of the stabilising zones according to the invention. In fact, the bandage material in this known bandage consists of a foamed material such as is used for diving suits. The bandage which must be adapted to the wearer in each case is cut from a piece of material and is to be bonded along a longitudinal seam to form a tubular body. The stiffening bands which are to be bonded to the outside of the foamed material reinforce the bandage over its entire surface. They serve thus exclusively to increase the overall stability and not—as in the invention—to support selected parts of the joint, which are in particular need of support.

Preferred illustrative embodiments are to be found in the dependent claims.

An illustrative embodiment of the subject of the invention is described below, with reference to the attached drawing in which.

Figure 1:
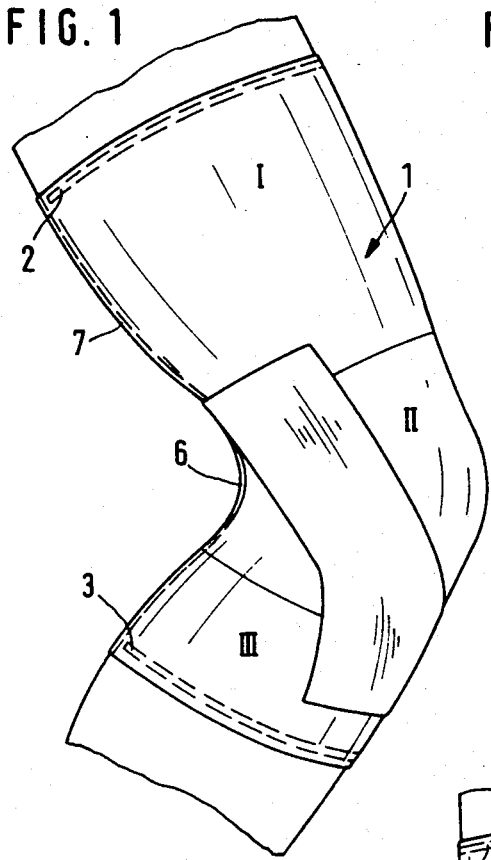
FIG. 1 shows a simplified side view of the bandage fixed to the knee.
Figure 3:
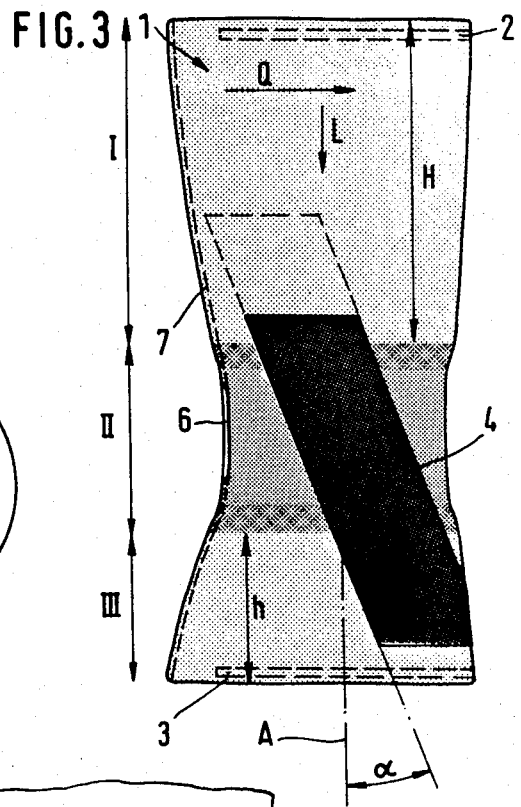
FIG. 3 shows the bandage taken off from the knee, viewed from the side.
Figure 2:
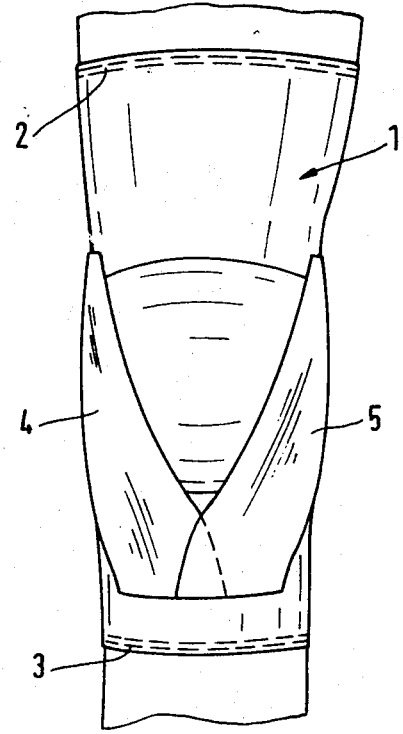
FIG. 2 shows the corresponding front view.

The knee bandage shown in FIGS. 1 to 3 has a tubular base body 1 which can be made from an elastic textile material by knitting, warp-knitting or weaving or also by another method and is elastically stretchable both in the longitudinal direction (arrow L in FIG. 3) and in the transverse direction (arrow Q). Possible starting materials are the known textiles produced on the basis of rubber or plastic. For example, Rhovyl yarn manufactured by Rhône-Poulenc has proved to be particularly suitable, but the invention is not at all intended to be restricted to this yarn or even to similar yarns.

As is also indicated, in particular in FIG. 3, three sections can be distinguished in the knee bandage shown, namely an upper section I lying against the thigh, a middle section II surrounding the knee joint, and a lower section III lying against the lower leg. For reasons of secure adhesion, the upper section I is preferably chosen to be considerably longer than the lower section III. In a preferred embodiment, the length H of the upper section is about 1.4 to 1.6 times the length h of the lower section III.

Moreover, the middle section II which surrounds the injured knee has, under the same loading, 2 to 10 times the elastic stretch of the two adjacent sections I and III. The increased tensile stretch, effective in both the directions Q and L, takes the natural function of the knee joint into account, the wearing comfort of the bandage being preserved and the desired position of the bandage being ensured by virtue of the two adjacent sections I and III, even during movement of the knee or prolonged rhythmical movement. Two holding strips 2 and 3 which are fixed—for example glued—to the inside of the two rim parts and extend over at least a part of the total circumference, provide additional security against the undesired sliding of the bandage, which is inevitable with the known bandages, in particular during prolonged sporting activities. In a preferred embodiment, these holding strips, preferably consisting of silicone rubber, are relatively flat bands of about 1 to 2 mm thickness and 5 to 10 mm height. As tests have shown, the strips securely hold the bandage in its optimum position, even during prolonged jogging. In many cases, even the fitting of only one, upper holding strip 2, should suffice.

The bi-directional elasticity of the material or knitting, already mentioned, also makes a further contribution to the sliding resistance.

In order to stabilise the knee joint even further, in particular with respect to undesired lateral movement, stabilising strips 4 and 5 are fitted to each flank of the knee bandage. These two strips, consisting likewise of an elastic textile material which is preferably relatively densely woven, knitted or warp-knitted and is also bi-directionally elastic, have, according to the illustrative embodiment shown, a straight-line shape and form, with the main axis A of the bandage, an angle of inclination α between 15° and 45°, which angle is about 30° in the preferred embodiment. In the front view according to FIG. 2, the two strips 4 and 5 thus approximately form a V, the crossing point of the strips being located in the central region below the knee joint. The length of the strips can be adjusted to the particular requirements, but it should prove in general to be advantageous to draw the upper section of the strip—as indicated by broken lines in FIG. 3—relatively far upwards. This results in good stabilisation, in particular against "rotation" of the knee in a horizontal plane located transversely to the axis A.

In addition to the desired warming action, the arrangement described thus provides excellent external stabilisation of the passive structures of the ligament system of the capsula of the knee, the warming and compressive action on the thigh improving the active stabilisation of the musculature.

The V-shaped stabilisers 4 which, if appropriate, can be reinforced by silicone rubber, limit the undesired pendular movements of the knee, which can lead to a traumatisation of the ligament structures of the capsula. The natural, physiological movement excursions are not impeded by the bandage described.

Due to the use of material of different elasticity (stretchability or tensile strength), the physiological knee function is assisted and excessive traumatising movement excursions are braked.

The tubular base body 1 can be produced on circular knitting machines or flat knitting machines. In the latter case, it is provided with a longitudinal seam 7. To protect the adjoining tissue structures of the leg, this seam is then preferably flush with the inside of the adjacent part of the bandage, any super elevation being displaced to the outside.

The wearing comfort of the bandage is further improved by the provision of a slot 6 fixed in the region of the hollow of the knee, which slot extends over a height of between 15 and 50 mm and is preferably located within the seam 7. When the knee is bent, this slot 6 opens wider and thus prevents undesired formation of creases.

Moreover, the knee bandage described has a considerably greater overall length than the known bandages, and this also contributes to the resistance to sliding, support and better warming.

The illustrative embodiment described can be modified by those skilled in the art in various ways within the scope of the concept of the invention. Thus, for example, it is possible for the stabilising zones 4 to be sewn on, welded on or glued on, or to be formed by a multiplicity of stabilising filaments which are entwined with the fabric of the knee bandage in the particular stabilisation zone. The stabilisation can also be obtained by impregnation with a special material.

The different elastic stretch of the zones I and III relative to the central zone II can be obtained, for example, by using a denser type of knitting, that is to say more fibre material per unit area, during the manufacture, or by using other materials or a greater variety of materials. Due to this different elastic stretch, sliding of the bandage with a bent—and hence longer—knee is avoided, since the central zone II can yield by virtue of its greater flexibility, whilst the rim zones I and III retain their holding function.

Figure 4:
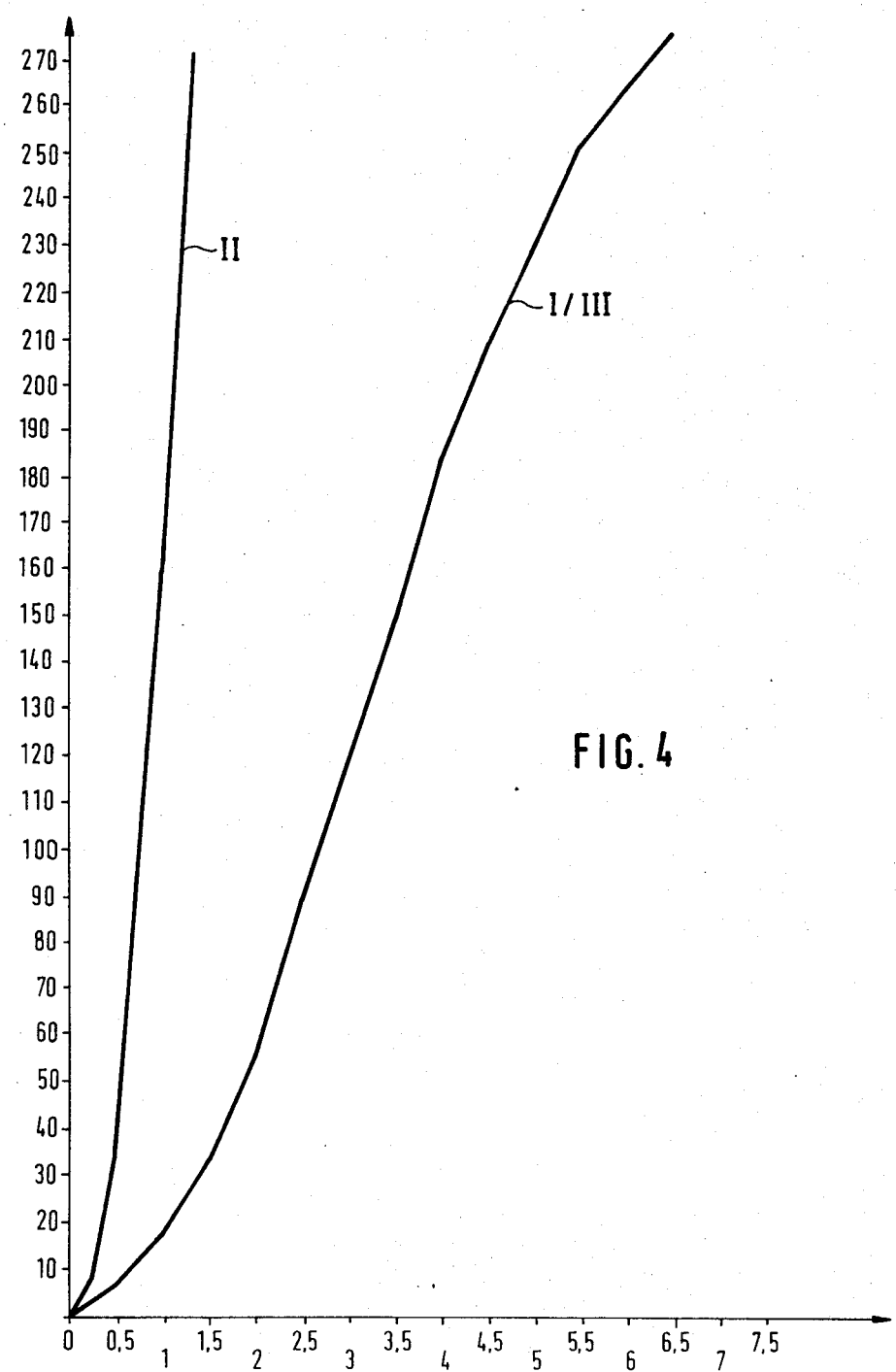
FIG. 4 shows a load/stretch diagram.

The load/stretch diagram according to FIG. 4 illustrates, by reference to an example, the different elastic stretch of the two rim zones I and III on the one hand and the central zone II on the other hand. It is clearly evident that the central section II, in the entire possible load range, has several times the stretch for the same increase of load.

We claim:

1. Knee bandage having a tubular base body which consists at least partially of an elastic textile material and comprises a central region which is to be laid against a knee joint, as well as two edge sections which adjoin this central region on both sides and the stretch properties of which differ from those of the central region, characterised in that, when the central region (II) and edge sections (I, III) are equally loaded, the central region (II) has an elastic stretch in the longitudinal and transverse directions which is at least 100% greater than that of the edge sections (I, III), that two zones (4) for stabilising the joint flanks are provided on the base body (1), which zones are each inclined relative to the longitudinal centre line (A) of the base body by an angle of 15°-45° and are arranged, on the one hand, to converge towards one another up to a region on the base body located below the position to be envisaged for the knee joint and, on the other hand, to extend beyond the knee region, and that at least that edge section (I) which adjoins the central region above the knee region is provided on the inside of its upper edge part with a holding strip (2) made of material which is resistant to sliding.

2. Knee bandage according to claim 1, characterised in that a holding strip (3) preferably consisting of a silicone rubber is arranged on the inside of the upper edge part and on that of the lower edge part.

3. Knee bandage according to claim 1, characterised in that the region of the hollow of the knee has a slot-shaped recess (6) which extends at most over the height of the central region (II).

4. Knee bandage according to claim 3, characterised in that the slot-shaped recess extends over a height of between 15 and 50 mm.

5. Knee bandage according to one of claim 4, characterised in that the said stabilising zones (4) extend in a straight line and, in a front view of the knee bandage, at least approximately in the form of a V.

6. Knee bandage according to one of claim 5, characterised in that the stabilising zones (4) are formed by bands which are sewn on or glued on.

7. Knee bandage according to claim 6, characterised in that the bands are reinforced by an impregnation with silicone rubber.

8. Knee bandage according to one of claim 1, characterised in that the stabilising zones (4) are formed by a multiplicity of stabilising filaments which are interwoven, in the particular stabilising region, with the fabric of the knee bandage.

9. Knee bandage according to one of claim 1, characterised in that its material in the region of the stabilising zones (4) is impregnated with a natural or synthetic rubber.

10. Knee bandage according to one of claim 9, characterised in that the stabilising zones (4) are inclined relative to the main axis of the knee bandage by 25° to 35°, preferably about 30°.

11. Knee bandage according to one of claim 10, characterised in that its upper section (I) lying against the thigh is at least 50% longer than the lower section (III) facing the lower leg.

12. Knee bandage according to one of claim 11, characterised in that at least its major part consists of a natural or synthetic material having a warming action.

* * * * *